United States Patent
Butzine et al.

(10) Patent No.: US 7,261,465 B2
(45) Date of Patent: Aug. 28, 2007

(54) PARK SENSOR MECHANISM FOR PORTABLE DIGITAL X-RAY DETECTOR ON MOBILE DIGITAL RADIOGRAPHY

(76) Inventors: Jonathan M. Butzine, 200 Glenwood Rd., Oconomowoc, WI (US) 53066; Jon C. Omernick, 2617 N. 88th St., Wauwatosa, WI (US) 53226; Sabih Q Zaman, 13330 W. Bluemound Rd. #1, Elm Grove, WI (US) 53122

( * ) Notice: Subject to any disclaimer, the term of this patent is extended or adjusted under 35 U.S.C. 154(b) by 47 days.

(21) Appl. No.: 11/324,473

(22) Filed: Dec. 31, 2005

(65) Prior Publication Data

US 2007/0153980 A1    Jul. 5, 2007

(51) Int. Cl.
*H05G 1/02* (2006.01)
(52) U.S. Cl. ............ 378/198; 378/98.8; 378/189
(58) Field of Classification Search ............ 378/91, 378/98.8, 102, 114–117, 197, 198, 189, 210; 250/370.09
See application file for complete search history.

(56) References Cited

U.S. PATENT DOCUMENTS

| 7,109,491 B2* | 9/2006 | Shinden | 250/370.09 |
| 7,197,112 B2* | 3/2007 | Maschke | 378/91 |
| 2006/0070384 A1* | 4/2006 | Ertel | 62/3.3 |

* cited by examiner

*Primary Examiner*—Jurie Yun
(74) *Attorney, Agent, or Firm*—Peter Vogel; Carl Horton; Ellis B. Ramirez (57) ABSTRACT

Systems, methods and apparatus are provided through which the presence of a portable detector in a parking mechanism of mobile digital radiography system is used to change the operating mode of the portable detector and a mobile X-Ray system. An existing mobile digital X-Ray imaging system may be retrofitted with parking sensor mechanism for determining the proximity of the portable detector to the mobile digital radiography system. Also provided is a method for controlling a mobile digital imaging system having a mobile X-Ray base and having a parking mechanism for holding a detachable detector. Upon detecting the presence of the detachable detector in the parking mechanism a control signal is generated to alter the speed of the mobile unit and the power consumption status of the detachable detector.

17 Claims, 10 Drawing Sheets

PARK SENSOR MECHANISM FOR PORTABLE DIGITAL X-RAY DETECTOR ON MOBILE DIGITAL RADIOGRAPHY

FIELD OF THE INVENTION

This invention relates generally to Mobile Digital Radiography (Mobile DR) systems, and more particularly to a park sensor mechanism for determining the position of a portable detector relative to the mobile radiography unit.

BACKGROUND OF THE INVENTION

Many medical devices serve the portable healthcare and emergency response markets. Examples of these devices are heart-rate monitors, glucometers, electrocardiogram (ECG) monitors, ultrasound imaging devices, and diagnostic medical imaging devices such as digital radiographic detectors. Regardless of the application, these devices must be small, and lightweight to provide the user of the device with optimum mobility and ease of use. However, the requirements necessary to achieve portability result in severe constraints on space, weight and power dissipation causing an increase in the amount of heat energy generated by the components of the medical device. The primary sources of heat are the various integrated circuit components, and rechargeable batteries that power the device when in use or when battery charging takes place. The net result is that the heat contributes to an overall rise in temperature with both application and structural effects on the medical device. Structural effects or excessive heat generated by small portable electronic devices reduces battery life, reduces component life, reduces the reliability of the device, and increases device failure.

In diagnostic medical imaging devices the problem of heat generation is a greater concern due to high power requirements, usage of complex circuitry for optimal performance that is highly sensitive to heat, and patient safety. In particular, while the high power and high circuit density required by the portable battery powered diagnostic medical imaging devices further exacerbate the problem of heat generation, these devices must satisfy certain medical safety requirements regulating the maximum external surface temperature of the device to insure patient safety. Present medical safety requirements regulating temperature mandate that the maximum allowable external surface temperature of a medical device (i.e., the "skin" temperature) not exceed approximately 40 degrees ° C. (104 degrees Fahrenheit), thereby ensuring that contact with a patient will not result in patient discomfort or burning. More specifically, there are regulations and rules regarding the temperature of medical devices, such as IEC 60601-1 promulgated by the International Electrotechnical Commission. These regulations are known to the practitioners of the art.

In the case of digital radiographic or digital x-ray, the electronics in the detector generates a significant amount of heat during image acquisition, due to their electrical power consumption, but consumption can be optimized when no image is being taken. These devices include a source for projecting an x-ray beam toward an object to be analyzed, such as a medical patient. After the beam passes through the patient, an image intensifier converts the radiation into a signal. With solid state digital x-ray detectors, the photodiode detector elements produce electrical signals that correspond to the brightness of the picture element in the x-ray image projected onto the detector. The signals from the detector elements are read out individually and digitized for further image processing, storage and display, typically by a computer. However, to achieve the required image quality, some time is required for electronic signal levels to stabilize between the image detector being restored to full power and acquisition of an image. This stabilization time to interfere with the process of acquiring the image is undesirable because the patient may be in an uncomfortable position, required to hold their breath for the image, or other reasons.

To add to the complexity of the problem the imaging performance characteristics of the detector vary with the temperature of the panel and the temperature of the pixel array. For optimum imaging performance, the panel temperature must remain within a range of temperatures. Techniques utilizing higher x-ray power and longer exposures are in demand in order to provide better images. At full power, the electronics of the detector consume sufficient power and generates sufficient heat to require a thermal management control subsystem to maintain the panel within the optimum imaging temperature range. Previous attempts at developing cooling systems to remove the heat energy from the relatively high-density packaging of radiographic digital image detectors have primarily used thermal convection systems. These systems move large volumes of heat absorbing air or fluid through the radiographic digital image detector to remove the heat energy created by operation of the device. This large volume requires open spaces around the digital radiographic detector. The necessity of these open spaces limits the overall density of the storage devices relative to the volumetric space of the storage system. However, this technique depletes the finite amount of energy especially in a portable device.

For the reasons stated above, and for other reasons stated below which will become apparent to those skilled in the art upon reading and understanding the present specification, there is a need in the art to manage the power consumed by portable digital detector and to manage the energy losses due to heat generated by the portable digital detector. Additionally, there is a need to limit the movement of the mobile radiography unit if the detector is not stowed away in the unit.

BRIEF DESCRIPTION OF THE INVENTION

The above-mentioned shortcomings, disadvantages and problems are addressed herein, which will be understood by reading and studying the following specification.

The invention is directed to a method and apparatus for managing the power level of a portable digital detector based on its position relative to a mobile digital radiography system.

In one aspect, existing mobile digital X-Ray imaging systems are retrofitted with a parking sensor mechanism for determining the proximity of the portable detector to the mobile digital radiography system.

In another aspect, mobile digital imaging system has a mobile X-Ray base with detachable detector. The system is comprised of a parking mechanism for holding the detachable detector and a unit for detecting the presence of the detector in the parking mechanism. Based on the position of the portable detector a controller issues a control signal to reduce the speed of the mobile unit and allow the portable detector to operate at an "ON" state. If the position of the detector is within close or resting at the parking mechanism then the mobile unit is permitted to operate at full speed and the portable detector is set to either an "OFF" or "IDLE" position.

In yet another aspect, a method for controlling a mobile digital imaging system having a mobile X-Ray base and having a parking mechanism for holding a detachable detector. Upon detecting the presence of the detachable detector in the parking mechanism a control signal is generated to alter the speed of the mobile unit and the power consumption status of the detachable detector.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. Further the term portable detector, detachable detector, detector, portable digital X-Ray detector as used herein refer to a detector that can be easily moved by a user or operator and its inclusive of X-Ray, ultrasound, or any other patient monitoring device that is movable by a user whether tethered or un-tethered to a medical unit. The following detailed description is, therefore, not to be taken in a limiting sense.

The detailed description is divided into five sections. In the first section, a system level overview is described. In the second section, apparatus of embodiments are described. In the third section, methods of embodiments are described. In the fourth section, the hardware and the operating environment in conjunction with which embodiments may be practiced are described. Finally, in the fifth section, a conclusion of the detailed description is provided.

System Level Overview

Figure 1:
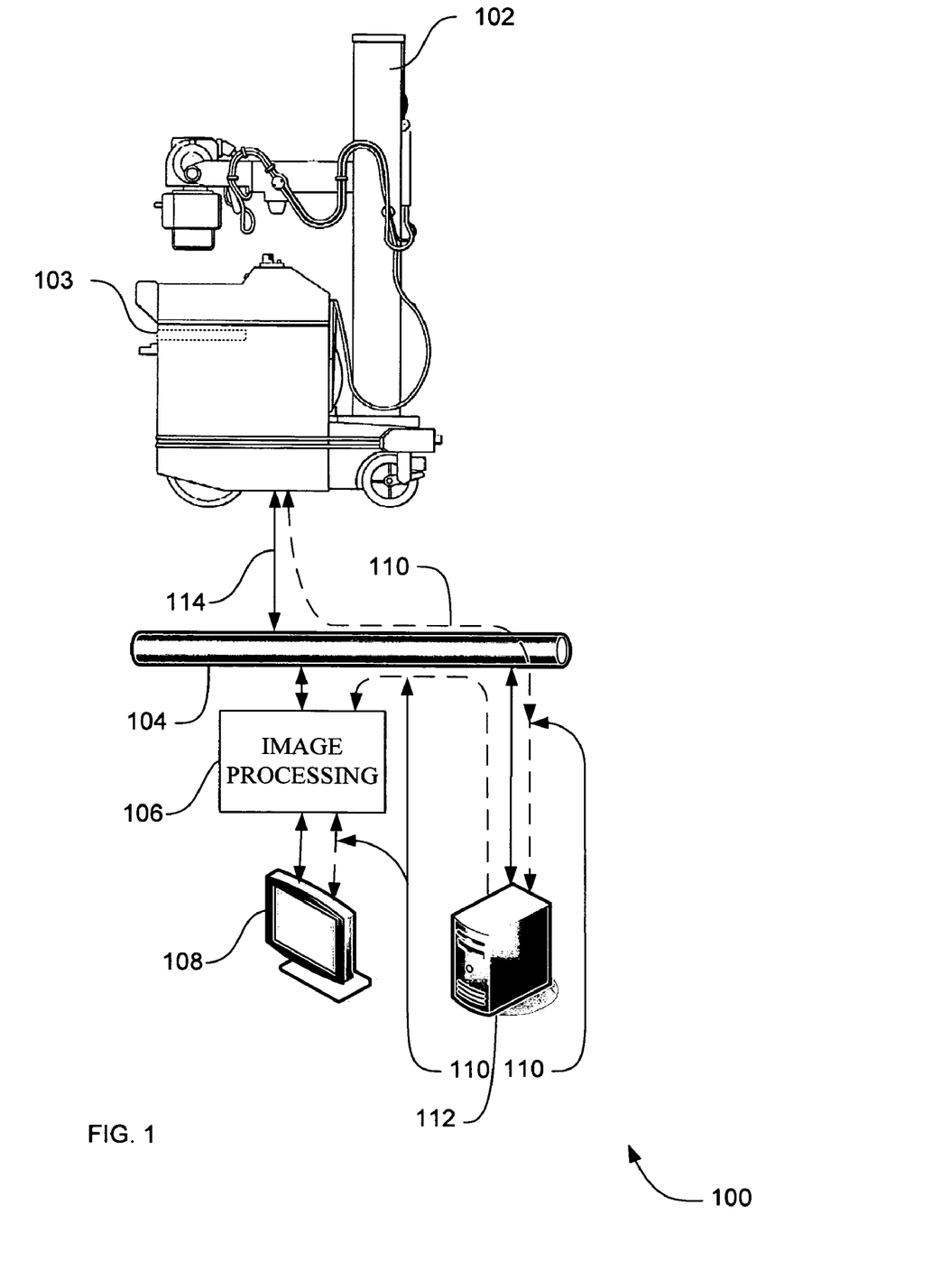
FIG. 1 is a block diagram that provides an overview of a system to capture a digital image at a mobile medical digital X-Ray imaging system and to display the digital image.

FIG. 1 is a block diagram that provides an overview of a system to capture a digital image at a mobile medical digital X-Ray imaging system and to process the digital image. System 100 solves the need in the art to display an image from a mobile medical digital X-Ray imaging system that does not significantly increase the power consumption of the portable digital detector and limits movement of the mobile medical digital X-Ray imaging system when the portable detector is being operated by a technician.

System 100 includes a mobile digital imaging system 102, such as the mobile X-Ray digital imaging system shown in FIG. 1. System 100 also includes drawer 103. The mobile digital imaging system 102 is operably coupled to a network 104, such as an Ethernet compliant network shown in FIG. 1. In some embodiments, the network is a network that is specifically adapted to function as a medical imaging network.

System 100 also includes an image processing system 106 that has a display device, such as image processing system that includes display device 108.

Figure 3:
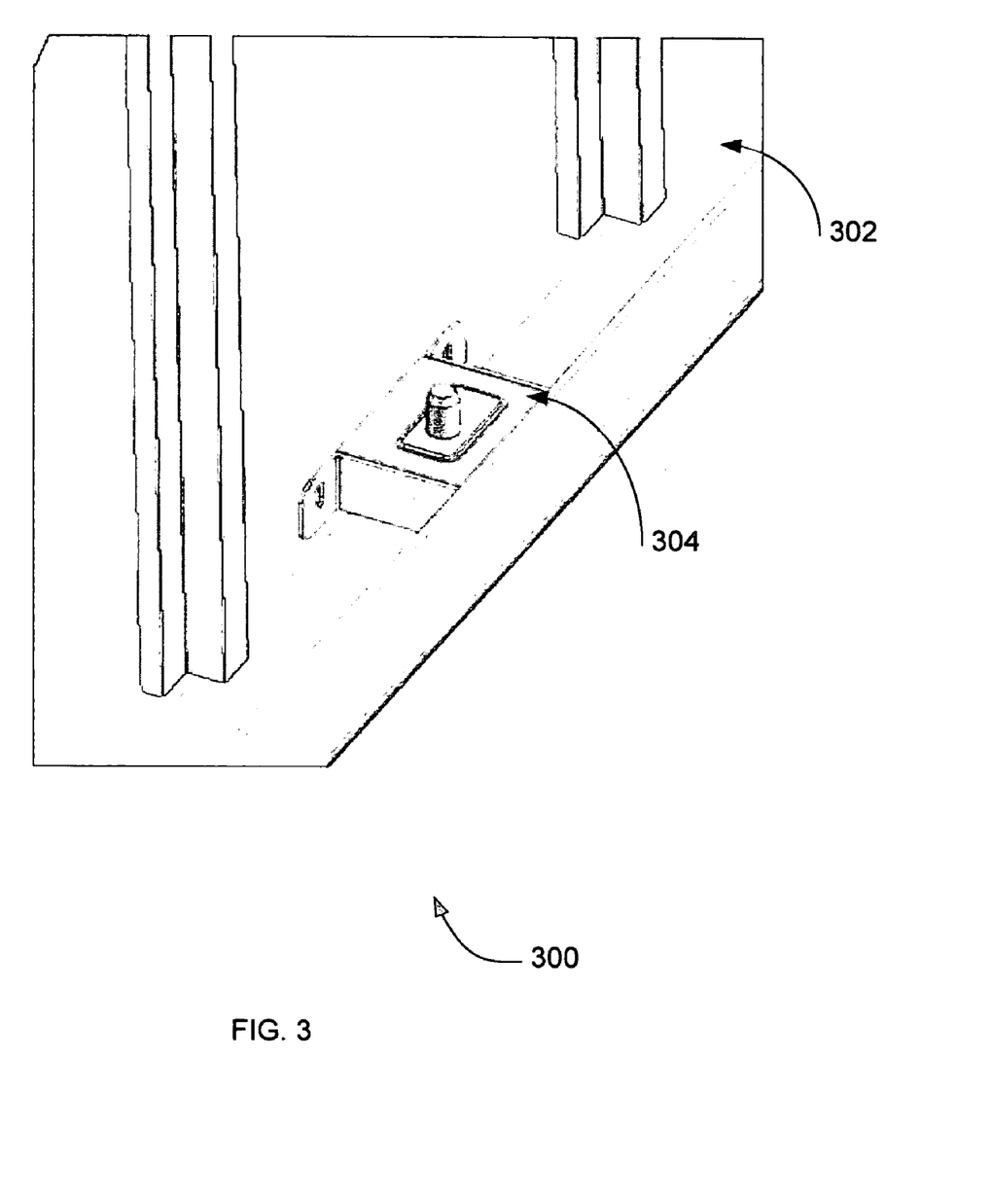
FIG. 3 is a view of the parking mechanism and sensor according to an embodiment.

The X-ray system preferably has a parking mechanism to hold a portable digital detector until it is needed by the operator, user, or x-ray technician. Such a parking mechanism preferably serves as the center of the X-ray system, from which the mobile digital radiography system or mobile digital radiography system units are allocated as required to the active X-ray radiation units. This parking mechanism may also serve as a supply and/or communication center. For this purpose the parking mechanism also has mechanical and IT interface devices, which correspond to interface devices of a mobile digital radiography system. These interface devices each comprise in particular at least one detector holder for a mobile digital radiography system or are each part of a detector holder for a mobile digital radiography system. The IT interface devices of a parking mechanism comprise in particular a link point for the efficient transmission of recorded image data from the mobile digital radiography system unit to the parking mechanism. This can be a wireless interface or tethered connection, so that the data can be transmitted during transportation of the mobile digital radiography system unit from the X-ray radiation unit to the parking mechanism. Alternatively another link point can also be used, e.g. an electrical or optoelectronic link point. The parking mechanism is preferably assigned one or a plurality of imaging systems, i.e. the parking mechanism is connected to one or a plurality of imaging systems or the parking unit comprises an imaging system or a plurality of imaging systems. An imaging system hereby preferably comprises an image data interface, an imaging system controller, an image processing unit and a display unit, e.g. a monitor or a display. The display unit preferably also serves, as described in more detail below, to show the position of the mobile digital radiography system units. The components of the imaging system are in particular connected to each other by means of a data or system bus. The imaging system is preferably connected via the image data interface to the parking mechanism and/or a data and image network, so that image data can also be displayed on other display units, which are for example remote from the imaging system. To supply a mobile digital radiography system unit with power, the mobile digital radiography system unit preferably has a battery unit. This battery unit can be charged with power via the above-mentioned interface device, when the mobile digital radiography system unit is located in a holder in the parking mechanism or an X-ray radiation unit (FIG. 3). Additionally or alternatively a mobile digital radiography system may have a power pack, a rechargeable power pack, a dedicated power supply at the place of deployment, or a connector for coupling to an electrical outlet.

After the mobile imaging system 102 captures a digital image, the digital image may be optionally transmitted to the network 104 along communication path 110. A server 112 on the network 104 receives the digital image and transmits the digital image along communication path 110 to an image processing system such as image processing system 106 having display device 108 for displaying the digital image in real time thus permitting instant review by a trained operator. Thus, displaying an image that is captured on the mobile digital imaging system 102 does not require a display device on the mobile digital imaging system 102.

System 100 provides a means of accessing and using the display and image processing capability of the network. Where the display and imaging capability of the network is significant, this is a capability of system 100. For example, when the network 104 has sophisticated abilities such as a network that provides interactive access to images encoded in accordance with the Digital Imaging and Communications in Medicine (DICOM) standard, or three-dimensional (3D) software tools to handle high exam volumes, large data sets and faster scan times, such as provided by the Advantage Imaging Network® or Advantage Workstation® manufactured by General Electric Healthcare of Waukesha, Wis. These capabilities are very expensive to provide in the mobile digital imaging system 102. However, where such sophisticated abilities are available to the mobile digital imaging system 102, it is considerably economical to operably couple the mobile digital imaging system 102 to the network, while also avoiding adding the weight, space requirements and power consumption requirements of the imaging apparatus that would provide that capability on the mobile digital imaging system 102. System 100 avoids having to provide sophisticated and expensive imaging processing and display functions in redundant and duplicate quantities.

A coupling 114 between the mobile digital imaging system 102 and the network can be accomplished in one of a number of means. For example, a wireless connection is implemented between the mobile digital imaging system 102 and the network. In some embodiments, a wired connection is implemented. In some embodiments, and coupling 114 includes the Internet.

While the system 100 is not limited to any particular mobile digital imaging system 102, network 104, image processing system 106, display device 108, communication path 110, server 112, or coupling 114, for sake of clarity a simplified mobile digital imaging system 102, network 104, image processing system 106, display device 108, communication path 110, server 112, and coupling 114 are described.

Figure 2:
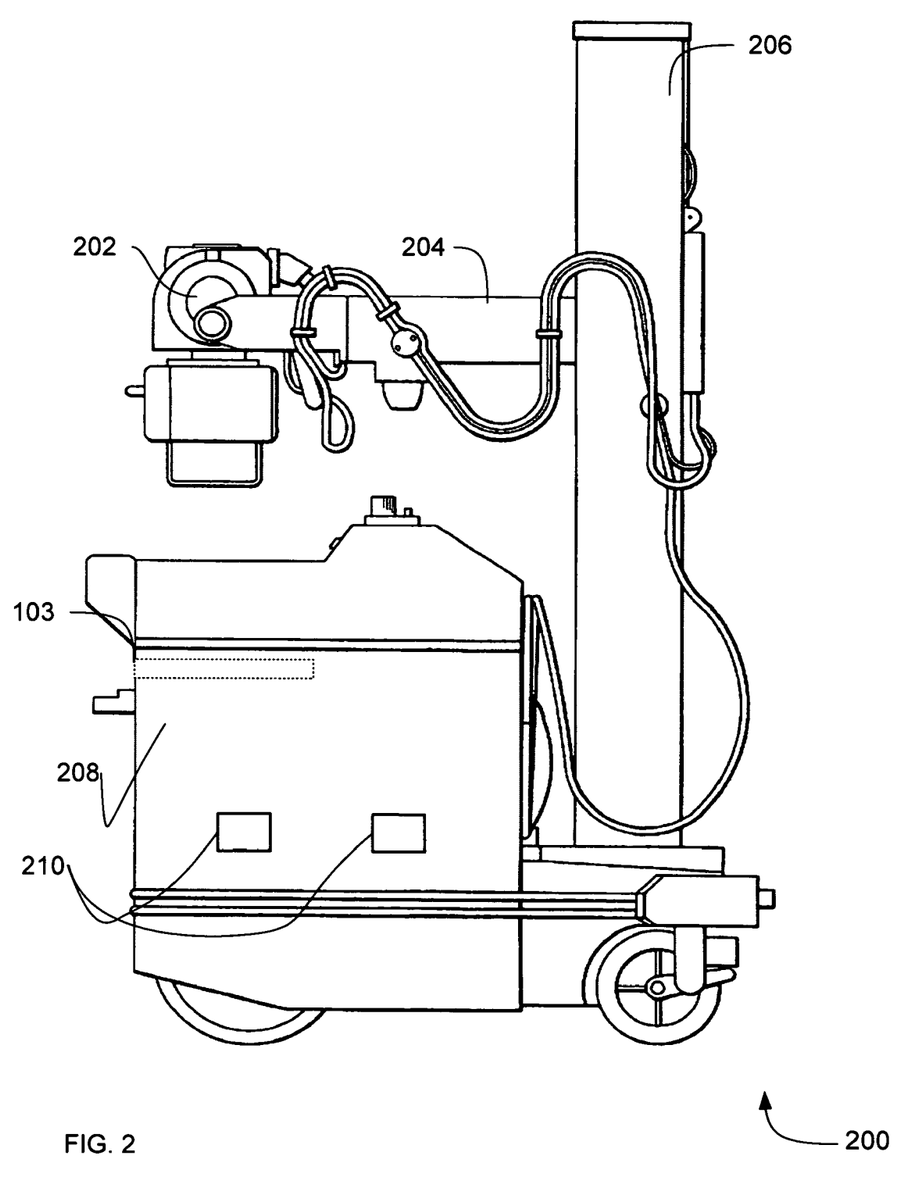
FIG. 2 is a side view of mobile digital X-Ray imaging system according to an embodiment having a plurality of network interfaces.

FIG. 2 is a side view of mobile digital X-Ray imaging system 200 according to an embodiment having a plurality of network interfaces. Apparatus 200 solves the need in the art to display an image from a mobile medical digital imaging system that does not significantly increase the cost, weight, size and power consumption of the mobile medical digital imaging system.

Mobile digital X-Ray imaging system 200 includes an X-Ray source 202 that is mounted to the end of a horizontal arm 204. The X-Ray source 202 is positionable over an area of concern on a patient. The X-Ray source 202 is typically mounted through a gimbal type arrangement in which a column 206 is required to rotate to move the X-Ray source from the park position on the mobile X-Ray unit base 208 to the appropriate position in order to take an X-Ray image of the patient.

Mobile digital X-Ray imaging system 200 also includes a plurality of network adapters 210. Two network adapters in the plurality of network adaptors 210 are shown in FIG. 2, but any number of network adapters more than one can be implemented. One of the network adapters 210 is conventionally is used to connect to an external digital X-Ray detector. One of the other additional network adapters 210 is used as an interface to an electronic system that is operable to display an image from the mobile digital X-Ray imaging system 200, such as system 100. At least one of the network adapters 210 is a conventional network adapter, such as an Ethernet adapter.

The graphical depiction of the size of the network adapters 210 is increased relative to the mobile digital X-Ray imaging system 200 in FIG. 2 in order to improve legibility of the network adapters 210. The actual network adapters are usually smaller in size relative to the mobile digital X-Ray imaging system 200.

In an alternative embodiment, mobile digital X-Ray imaging system 200 includes only one network adapter to communicate to the electronic system that is operable to display an image from the mobile digital X-Ray imaging system 200, such as system 100.

In one example where of the network adapters 210 are Ethernet network adapters, the Ethernet network adapter provides a connection to a mobile digital imaging system, such as the mobile digital imaging system 102 of FIG. 1 through an Ethernet compliant communication channel. In some embodiments, the Ethernet compliant communication channel couples to a router, that in turn in coupled to the Internet, that in turn is connected to a network, such as network 104 in FIG. 1 that provides display and processing apparatus and capability on a digital image that is captured by the mobile digital imaging system 102. In some embodiments, the Ethernet compliant communication channel is a direct wired connection to the network, such as network 104 in FIG. 1. As an alternative to Ethernet, other conventional network protocols can be used, such as LocalTalk that was developed by Apple Computer, Inc., token ring protocol that was developed by IBM, fiber distributed data interface (FDDI), and asynchronous transfer mode (ATM). In addition, any conventional network topology can be used, such as linear bus, star, tree, star-wired ring or dual ring.

Mobile digital X-Ray imaging system 200 shows a network adaptor for a wired Ethernet connector. However mediums other than wires can be implemented, such as wireless connection (e.g. infrared or radio) to couple or connect the mobile digital X-Ray imaging system 200 to a network.

FIG. 3 is a view of a parking mechanism for holding the portable digital detector when not in used. The parking mechanism 300 may be within the mobile radiography system 100, may be carried by the operator, or may be standard equipment at the point of deployment. The Inside the mechanism is a switch or proximity sensor 304 for ascertaining the position of the portable detector relative to the mobile digital radiography system or imaging system. Alternatively, the sensor could serve the additional purpose of holding the portable digital detector by equipping the portable detector with a sleeve, glove, or hole that would mate with the protruding switch 304 to hold the portable detector in place. The sensor could be a switch that utilizes mechanical, electromechanical, optical, capacitive, infrared, pressure or any other type of switch whether presently existing or to be developed in the future that can indicate a change in state.

Figure 4:
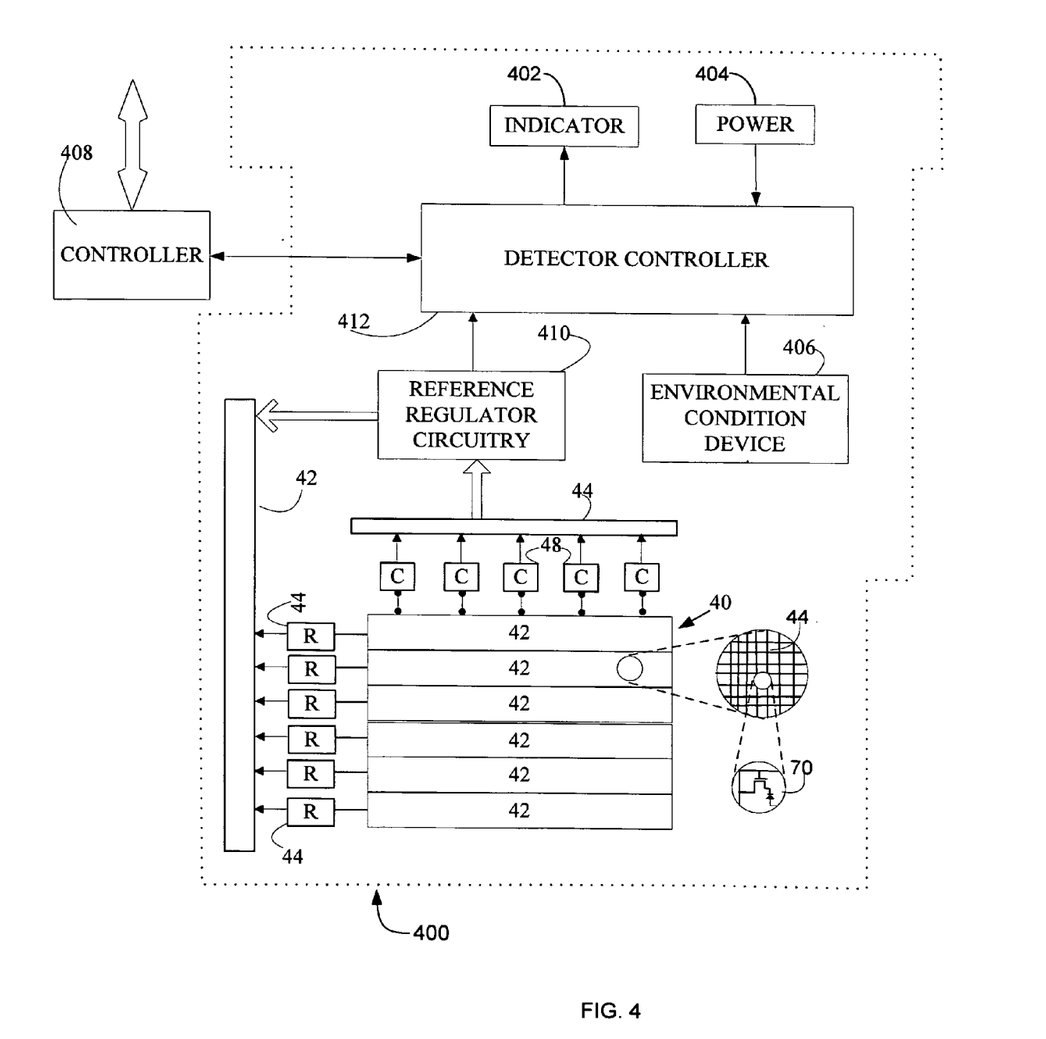
FIG. 4 is a block diagram of the hardware and operating environment of the radiographic detector.

FIG. 4 is a block diagram that illustrates detector 400. Embodiments are described as operating in a multi-processing, multi-threaded operating environment on a computer, such as computer 106 in FIG. 1 and FIG. 7. FIG. 4 is a diagrammatical representation of functional components of digital detector 400.

FIG. 4 includes a controller (Hereinafter referred as IDC) 408, which in some embodiments will be configured within a detector controller 412. IDC 408 includes a CPU or digital signal processor as described in FIG. 7, as well as memory circuits for commanding acquisition of sensed signals from the detector 400. In some embodiments, IDC 408 is coupled via two-way fiberoptic conductors, infrared interface, or wireless interface to detector control circuitry 412 within detector 400. IDC 408 thereby exchanges command signals for image data within the detector during operation.

Detector controller 412 circuitry receives DC power from a power source, represented generally at reference numeral 404. Detector controller 412 is configured to originate timing and control commands for row and column drivers used to transmit signals during data acquisition phases of operation of the system. Detector controller 412 therefore transmits power and control signals to reference/regulator circuitry 410, and receives digital image pixel data from circuitry 40. Additionally indicator 402 is coupled to detector controller 412 for displaying information such as operation and power status to the operator.

The controller 412 can be triggered through the IDC 408 or receive a signal as to the position of the detector relative to the parking mechanism to switch between power modes (OFF, IDLE, ON). The detector controller could use the status of the sensor switch in conjunction with historical or generally statistical data to infer whether the state of the detector is likely to change. The purpose of the indicator 206 is to convey to the user or operator the status of the detector as being "ON", "IDLE", or "OFF". The environmental condition device 406 monitors the detector battery status, detector error status, temperatures of other devices or room, diagnostics, internal temperature, voltage or state of the panel/detector can be attained in this manner. That is, the detector 400 may be commanded or contains internal control to transition between modes without a system trigger if an environmental condition goes beyond tolerances. In so doing, the internal detector temperature can be maintained by going between modes of operation. This requires a feedback loop either internal to the detector or remote to the imaging detector controller 412, computer 702, or image processor 106. In addition, a background process exists to periodically transition the detector between modes to assess information from the detector. That is, the detector could be interrogated by IDC 408 or any other external device to read the content of the environmental condition device 406 and then use the retrieved data as a condition for change between the modes of operation.

In a present embodiment, detector 400 consists of a scintillator that converts X-ray photons received on the detector surface during examinations to lower energy (light) photons. An array of photo detectors then converts the light photons to electrical signals, which are representative of the number of photons or the intensity of radiation influencing individual pixel regions of the detector surface. Readout electronics convert the resulting analog signals to digital values that can be processed, stored, and displayed, such as in a operator interface 722 or a display 108 following reconstruction of the image. In the particular embodiment illustrated in FIG. 4, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector. As also illustrated in FIG. 5, each pixel 54 is generally defined at a row and column crossing, at which a column electrode 48 crosses a row electrode 45 as shown in item 70.

Figure 5:
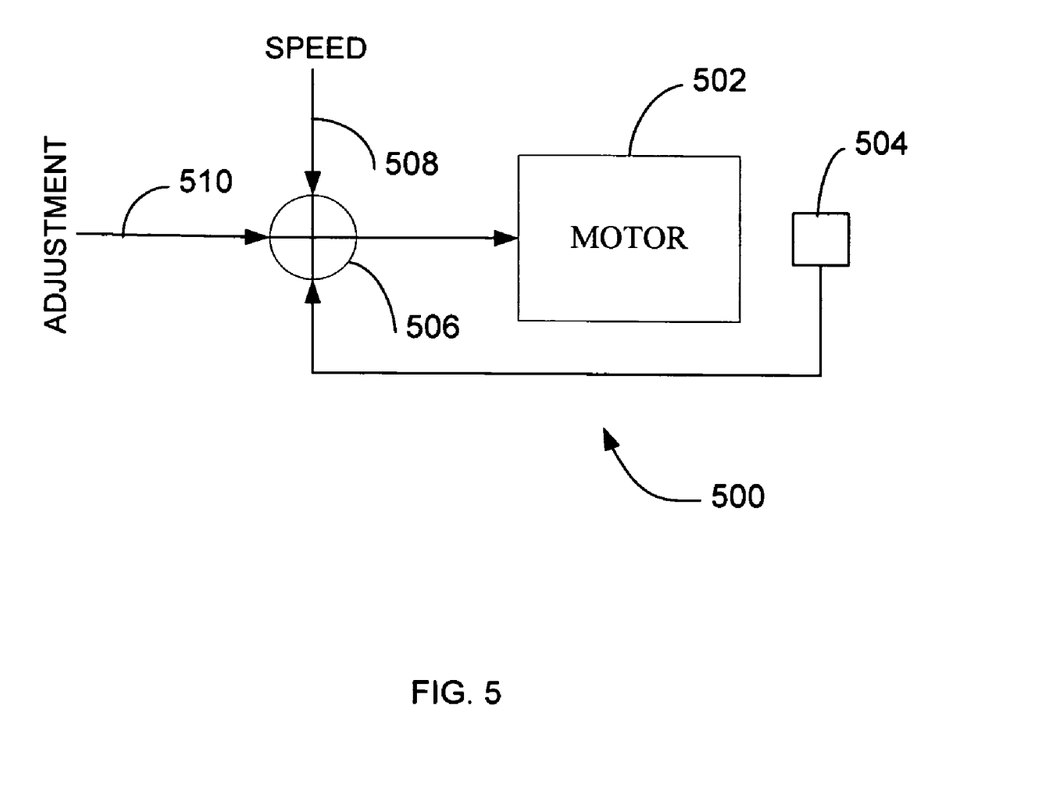
FIG. 5 is a diagram of apparatus, according to an embodiment for regulating an electric motor of a mobile digital radiography system.

In FIG. 5 a possible arrangement for regulating the speed of the mobile base is shown. The mobile X-Ray base or Mobile digital radiography system 200 is equipped with an electric power drive 502 for moving the system from location to location and is optionally provided with a speed measuring device 504 that is mounted adjacent rotating motor shaft (not shown). Device 504 is connected to a combiner 506 through an electrical conductor to provide a source of direct feedback of motor speed to regulate the speed of the motor when combined with an adjustment signal from controller 602. In some embodiments, the initial speed signal can be set to zero and the speed is regulated by the control signal 510 and the speed measuring device signal from device 504. The control signal could be set to a slow speed giving the operator an indication that the portable detector is in the parking mechanism. In the alternative, the speed measuring device 504 is removed and the speed regulating signals are a combination of the initial speed signal 508 and the adjustment signal 510 from the controller. In some embodiments, only the initial speed signal 508 and the adjustment signal 510 are used to regulate the speed of the electric power drive. The controller for producing the adjustment signal used to regulate the speed of the motor 502 is described with reference to system 600 at FIG. 6.

Apparatus of an Embodiment

Figure 6:
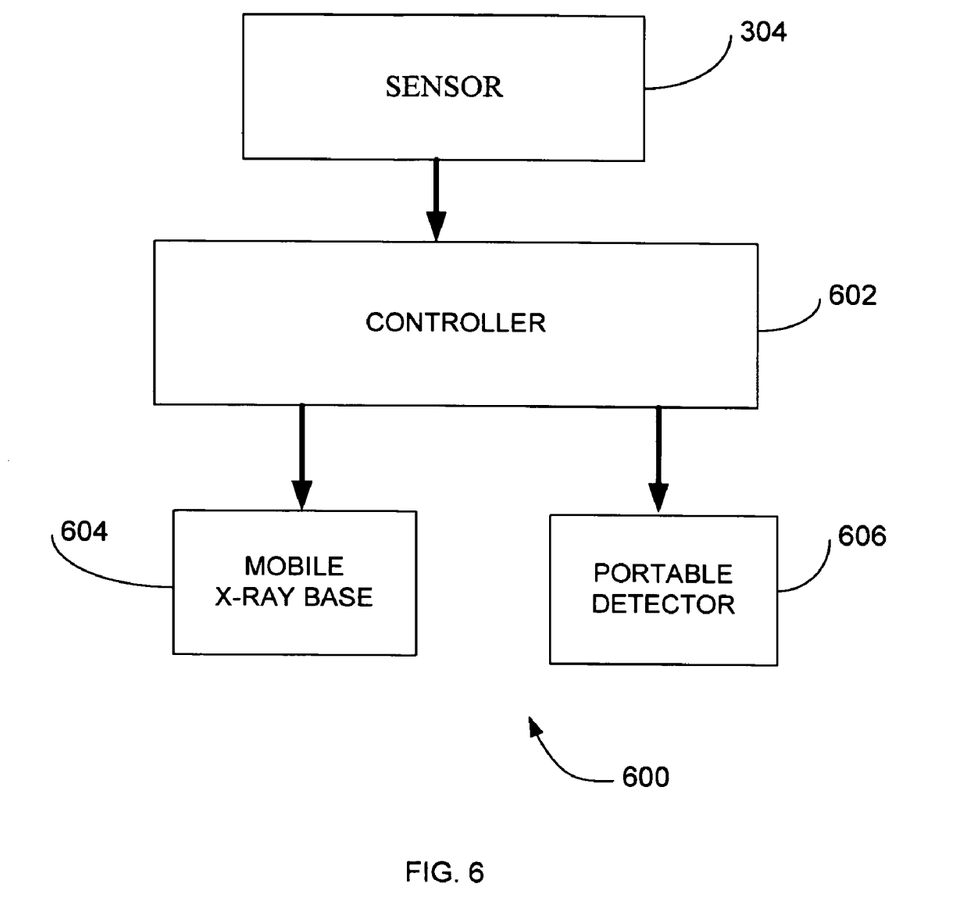
FIG. 6 is a view of a proximity detecting unit with controller for ascertaining the presence of a portable detector according to an embodiment.

In the previous section, a system level overview of the operation of an embodiment was described. In this section, the particular apparatus of such an embodiment are described by reference to a series of diagrams. FIG. 6 is a diagram of apparatus 600 according to an embodiment. Apparatus 600 solves the need in the art to change the power mode of a portable detector based on its position relative to the mobile base unit and to limit the movement of the mobile base unit when the portable detector is being used or is not in a resting position at the mobile base. In operation, when a portable detector is inserted into the parking mechanism 302, the sensor 304 detects the presence of the detector and serves a signal to the controller 602 that the detector is resting in the parking mechanism 302. Upon removal of the portable detector from the parking mechanism, the sensor 304 detects that the portable detector has been removed. The controller 602 is coupled to the sensor 304 and is programmed with logic that is best suited for the sensor 304 in used to detect the presence of the portable detector. For example, when the sensor 304 only has two states, i.e., either the portable detector is in or out of the parking mechanism, the controller can be programmed to act only on those two states to control the mobile unit and portable detector. However, when the sensor 304 includes additional information such as a predetermined distance from the parking mechanism the controller can alter the operating mode of the mobile unit and portable detector. For example, in a situation where the detector is out of the parking mechanism but not being used on a patient. In this situation, there would be a rise in temperature and a depletion of battery both leading to possible image degradation. In this type of arrangement, the controller could be programmed to keep the portable detector at a condition between "OFF and "ON" know as idle mode. This would require a sensor that provides the controller with information as to the location of the portable detector relative to the parking mechanism. It is conceivable to use a simple switch (on, off) and to program the controller with a prediction model based on prior use to determine when to engage the portable detector to an "ON" state. The controller 602 can be a microcomputer chip, microcontroller, or other available circuit providing a control function.

Methods of an Embodiment

In the previous section, apparatus of the operation of an embodiment was described. In this section, the particular methods performed by a client of such an embodiment are described by reference to a series of flowcharts.

Figure 8:
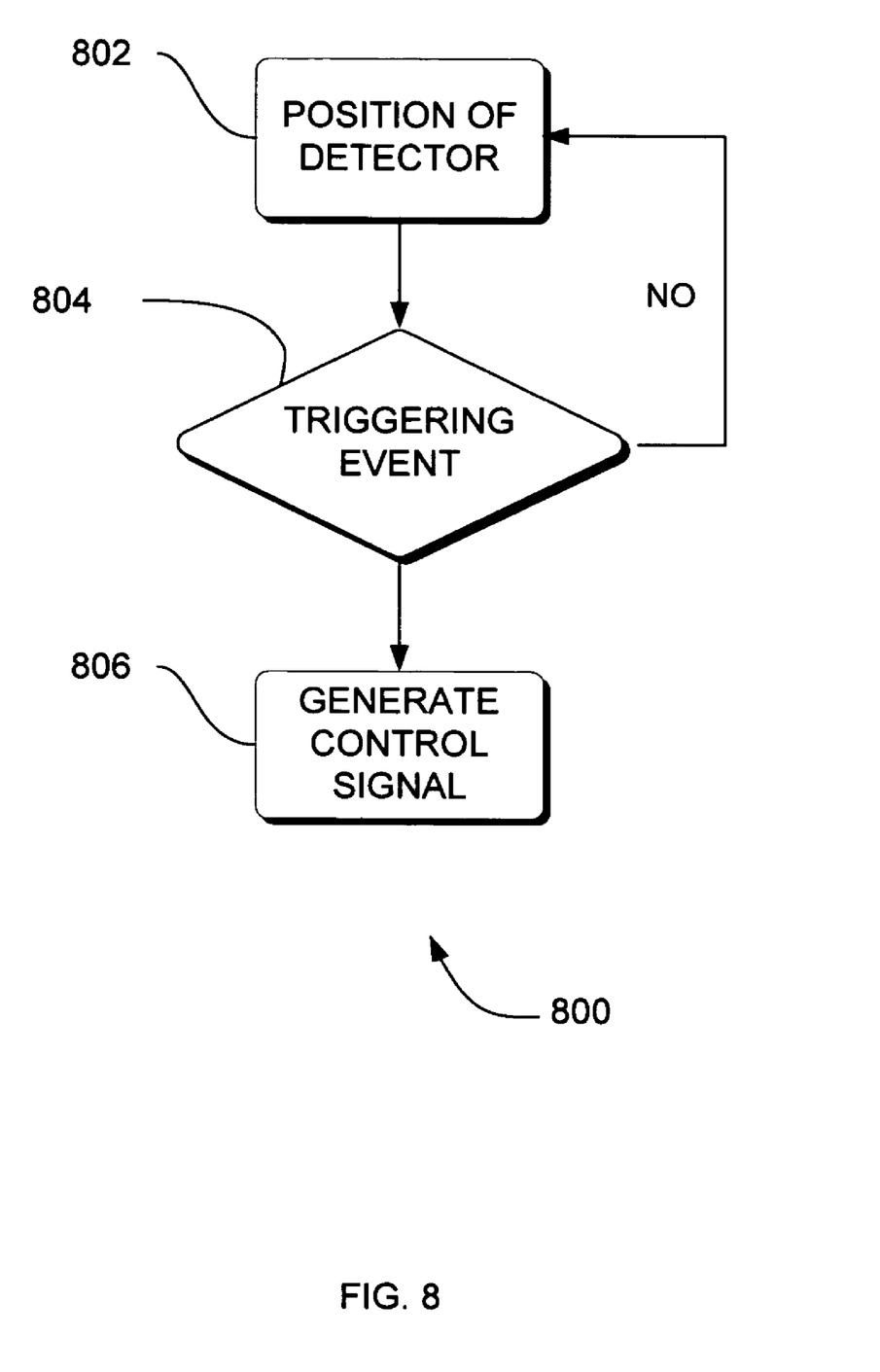
FIG. 8 is a flowchart of a method, according to an embodiment for generating a control signal.

FIG. 8 is a flowchart of a method 800 according to an embodiment. Method 800 solves the need in the art to display an image from a mobile medical digital X-Ray imaging system that does not significantly increase the power consumption of the portable digital detector and limits movement of the mobile medical digital X-Ray imaging system when the portable detector is being operated by a technician.

Method 800 begins with a determination of the position of the portable detector relative to the parking mechanism 302. As noted earlier the possible positions could be resting securely in the parking mechanism, within a predetermined distance from the parking mechanism, beyond a predetermined distance from the parking mechanism, or any other construct that can indicate the proximity of the portable detector from the parking mechanism. It is also possible to look at the position of the portable detector as being in used or not in used. When the detector is in the parking mechanism we can say that the portable detector is not in use. Once the position of the detector has being determined, control passes to action 804 for further processing.

In action 804 a triggering event is evaluated. The triggering event is transition from any previous position determined for the portable detector. For example, if the previous indication was that the portable detector was resting in the parking mechanism, i.e., parking sensor 304 would indicate an "ON" signal for a normally pushed in switch, and then a signal is received that would indicate that the portable detector was removed from the parking mechanism a triggering event has occurred. Likewise if the previous signal was that the portable detector was not in the vicinity of the parking mechanism, i.e. parking sensor 304 would indicate an "OFF" signal for a normally pushed out switch, a triggering event has occurred. If a triggering event does not occurred control passes back to determining the position of the detector until a triggering event is encountered. After a triggering event is encountered control passes action 806 for further processing.

In action 806 a control signal is generated. The control signal is based on the previous setting of the portable detector and the mobile X-Ray unit. As shown in the table STATES OF OPERATION the control signal would direct one of the enumerated conditions.

| STATES OF OPERATION | | |
|---|---|---|
| | MOBILE UNIT | PORTABLE DETECTOR |
| ON | SLOW SPEED | ON |
| OFF | FULL SPEED | OFF |
| PREDETERMINED DISTANCE | SLOW SPEED | IDLE |

Figure 9:
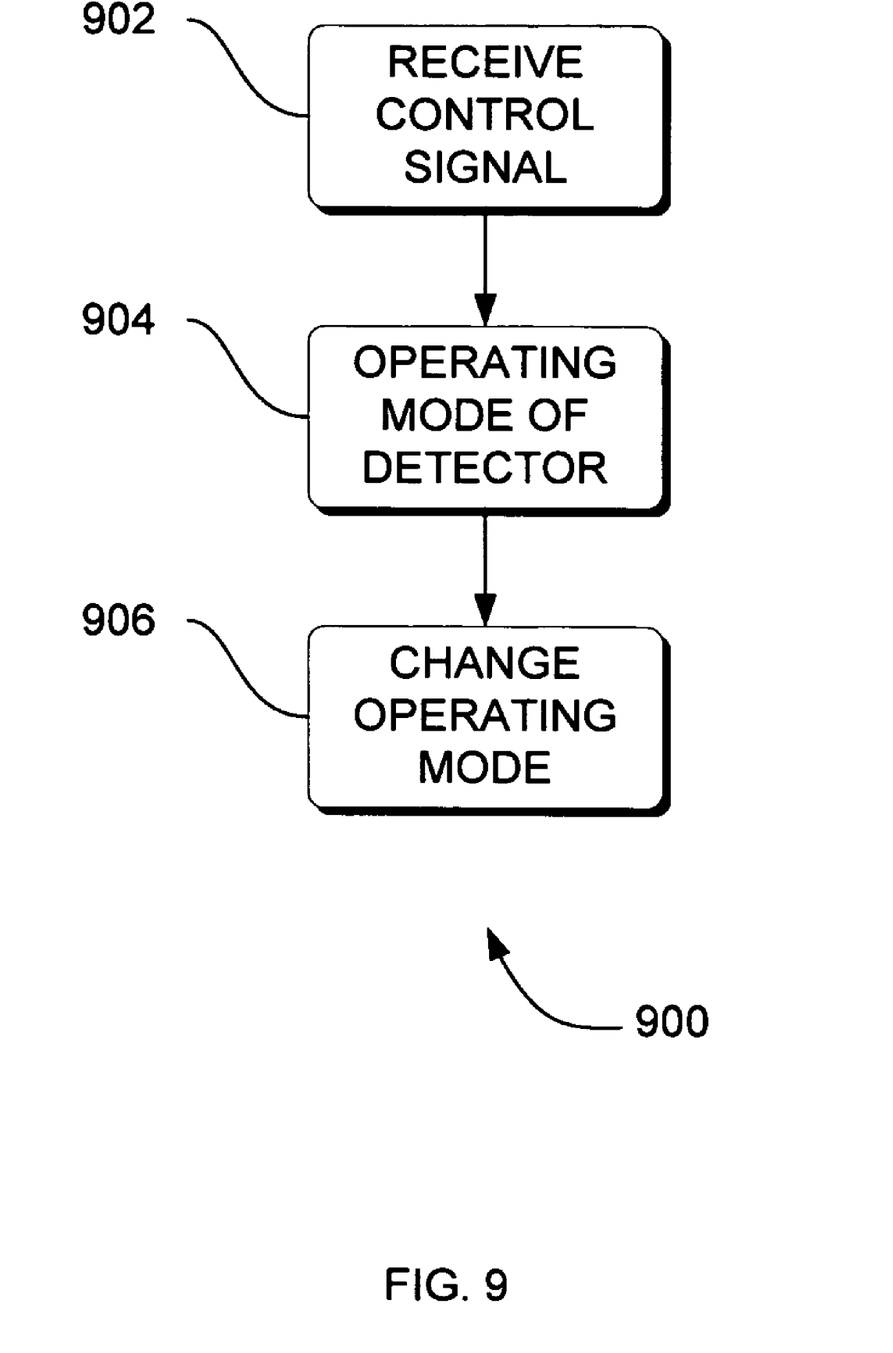
FIG. 9 is a flowchart of a method, according to an embodiment for changing the power level of a portable digital detector.

FIG. 9 is a flowchart of a method 900 according to an embodiment. Method 900 solves the need in the art to display an image from a mobile medical digital X-Ray imaging system that does not significantly increase the power consumption of the portable digital detector and limits movement of the mobile medical digital X-Ray imaging system when the portable detector is being operated by a technician.

Method 900 begins by receiving a control signal to change the operating mode of the portable detector. As noted earlier the operating mode is "OFF", "IDLE", "ON". Once the control has been received and process control passes to action 904 for further processing.

In action 904, the operating mode of the detector is determined from the received control signal. It should be noted, however, that the control signal could be a simple ON/OFF signal instructing the detector to switch from the current operating status. Once the operating mode of the portable detector is determined control passes to action 906 for further processing.

In action 906 the operating mode of the detector is switched in accordance to the received control signal.

Figure 10:
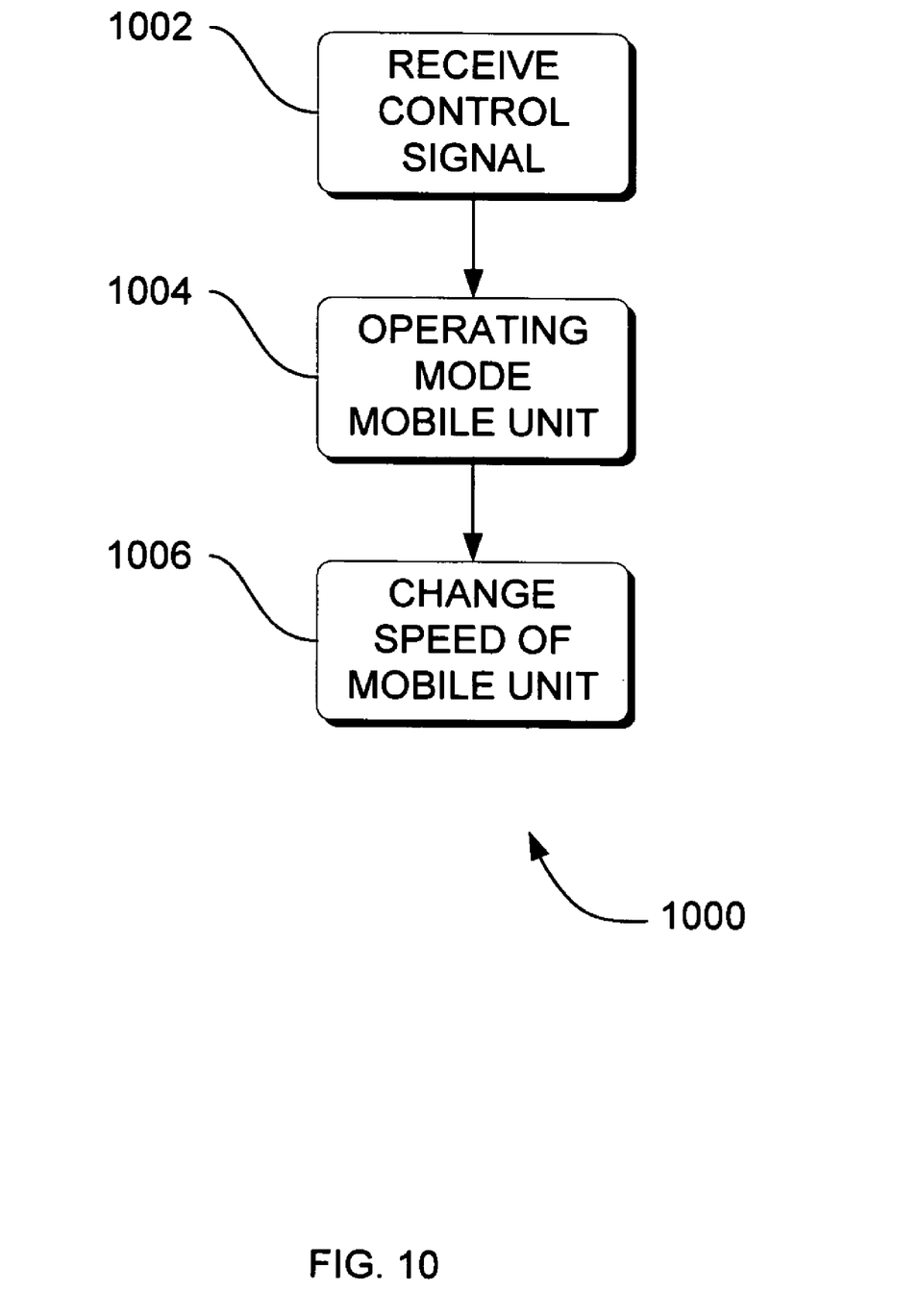
FIG. 10 is a flowchart of a method, according to an embodiment regulating the speed of a mobile unit.

FIG. 10 is a flowchart of a method 1000 according to an embodiment. Method 1000 solves the need in the art to display an image from a mobile medical digital X-Ray imaging system that does not significantly increase the power consumption of the portable digital mobile X-Ray base and limits movement of the mobile medical digital X-Ray imaging system when the portable mobile X-Ray base is being operated by a technician.

Method 1000 begins by receiving a control signal to change the operating mode of the mobile X-Ray base. As noted earlier the operating mode is "SLOW SPEED" or "FULL SPEED". Once the control has been received and process control passes to action 1004 for further processing.

In action 1004, the operating mode of the mobile X-Ray base is determined from the received control signal. It should be noted, however, that the control signal could be a simple ON/OFF signal instructing the mobile X-Ray base to switch from the current operating status. Once the operating mode of the mobile X-Ray base is determined control passes to action 1006 for further processing.

In action 1006 the operating mode of the mobile X-Ray base is switched in accordance to the received control signal.

Figure 7:
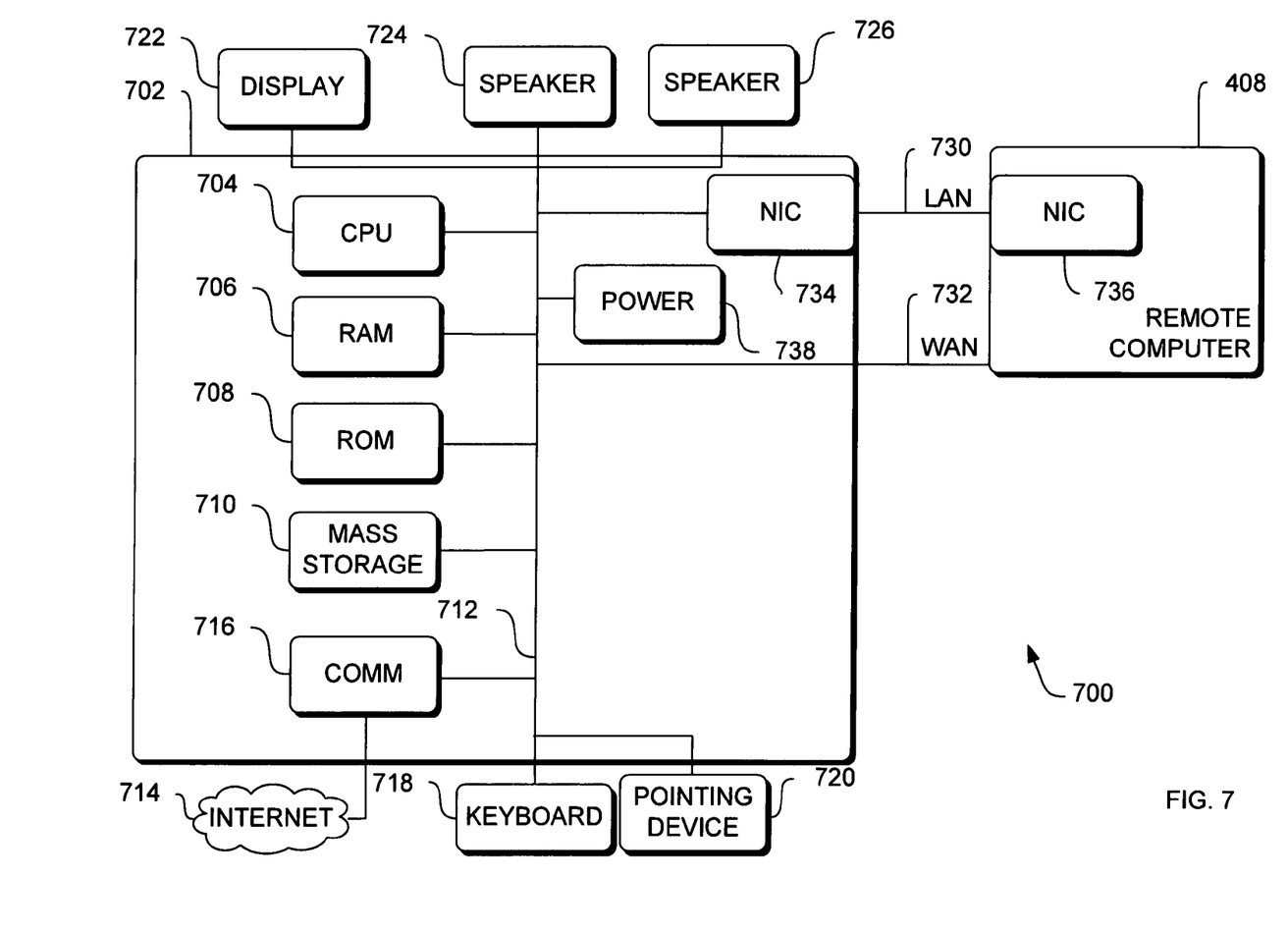
FIG. 7 is a block diagram of the hardware and operating environment in which different embodiments can be practiced.

In some embodiments, methods 800-1000 are implemented as a computer data signal embodied in a carrier wave, that represents a sequence of instructions which, when executed by a processor, such as processor 704 in FIG. 7, cause the processor to perform the respective method. In other embodiments, methods 800-1000 are implemented as a computer-accessible medium having executable instructions capable of directing a processor, such as processor 704 in FIG. 7, to perform the respective method. In varying embodiments, the medium is a magnetic medium, an electronic medium, or an optical medium.

Hardware and Operating Environment

FIG. 7 is a block diagram of the hardware and operating environment 700 in which different embodiments can be practiced. The description of FIG. 7 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 702 includes a processor 704, commercially available from Intel, Motorola, Cyrix and others. Computer 702 also includes random-access memory (RAM) 706, read-only memory (ROM) 708, and one or more mass storage devices 710, and a system bus 712, that operatively couples various system components to the processing unit 704. The memory 706, 708, and mass storage devices, 710, are types of computer-accessible media. Mass storage devices 710 are more specifically types of nonvolatile computer-accessible media and can include one or more hard disk drives, floppy disk drives, optical disk drives, and tape cartridge drives. The processor 704 executes computer programs stored on the computer-accessible media.

Computer 702 can be communicatively connected to the Internet 714 via a communication device 716. Internet 714 connectivity is well known within the art. In one embodiment, a communication device 716 is a modem that responds to communication drivers to connect to the Internet via what is known in the art as a "dial-up connection." In another embodiment, a communication device 716 is an Ethernet® or similar hardware network card connected to a local-area network (LAN) that itself is connected to the Internet via what is known in the art as a "direct connection" (e.g., T1 line, etc.).

A user enters commands and information into the computer 702 through input devices such as a keyboard 718 or a pointing device 720. The keyboard 718 permits entry of textual information into computer 702, as known within the art, and embodiments are not limited to any particular type of keyboard. Pointing device 720 permits the control of the screen pointer provided by a graphical user interface (GUI) of operating systems such as versions of Microsoft Windows®. Embodiments are not limited to any particular pointing device 720. Such pointing devices include mice, touch pads, trackballs, remote controls and point sticks. Other input devices (not shown) can include a microphone, joystick, game pad, satellite dish, scanner, or the like.

In some embodiments, computer 702 is operatively coupled to a display device 722. Display device 722 is connected to the system bus 712. Display device 722 permits the display of information, including computer, video and other information, for viewing by a user of the computer. Embodiments are not limited to any particular display device 722. Such display devices include cathode ray tube (CRT) displays (monitors), as well as flat panel displays such as liquid crystal displays (LCD's). In addition to a monitor, computers typically include other peripheral input/output devices such as printers (not shown). Speakers 724 and 726 provide audio output of signals. Speakers 724 and 726 are also connected to the system bus 712.

Computer 702 also includes an operating system (not shown) that is stored on the computer-accessible media RAM 706, ROM 708, and mass storage device 710, and is and executed by the processor 704. Examples of operating systems include Microsoft Windows®, Apple MacOS®, Linux®, UNIX®. Examples are not limited to any particular operating system, however, and the construction and use of such operating systems are well known within the art.

Embodiments of computer 702 are not limited to any type of computer 702. In varying embodiments, computer 702 comprises a PC-compatible computer, a MacOS®-compatible computer, a Linux®-compatible computer, or a UNIX®-compatible computer. The construction and operation of such computers are well known within the art.

Computer 702 can be operated using at least one operating system to provide a graphical user interface (GUI) including a user-controllable pointer. Computer 702 can have at least one web browser application program executing within at least one operating system, to permit users of computer 702 to access intranet or Internet world-wide-web pages as addressed by Universal Resource Locator (URL) addresses. Examples of browser application programs include Netscape Navigator® and Microsoft Internet Explorer®.

The computer 702 can operate in a networked environment using logical connections to one or more remote computers, such as remote computer 728. These logical connections are achieved by a communication device coupled to, or a part of, the computer 702. Embodiments are not limited to a particular type of communications device. The remote computer 728 can be another computer, a server, a router, a network PC, a client, a peer device or other common network node. The logical connections depicted in FIG. 7 include a local-area network (LAN) 730 and a wide-area network (WAN) 732. Such networking environments are commonplace in offices, enterprise-wide computer networks, intranets and the Internet.

When used in a LAN-networking environment, the computer 702 and remote computer 728 are connected to the local network 730 through network interfaces or adapters 734, which is one type of communications device 716. Remote computer 728 also includes a network device 736. When used in a conventional WAN-networking environment, the computer 702 and remote computer 728 communicate with a WAN 732 through modems (not shown). The modem, which can be internal or external, is connected to the system bus 712. In a networked environment, program modules depicted relative to the computer 702, or portions thereof, can be stored in the remote computer 728.

Computer 702 also includes power supply 738. Each power supply can be a battery.

CONCLUSION

A method and apparatus has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future sensing or switching devices, different radiography systems, and new portable detectors.

The terminology used in this application with respect to imaging detectors, mobile X-Ray systems is meant to include all portable detectors and X-Ray system environments and alternate technologies which provide the same functionality as described herein.

We claim:

1. A mobile digital imaging system, the mobile digital imaging system comprising:
   a mobile base with a detachable detector, wherein the mobile base has one or more drive speed;
   a parking mechanism for holding the detachable detector;
   a unit for detecting the presence of the detachable detector in the parking mechanism; and
   a controller coupled to the unit for detecting the presence of the detachable detector in the parking mechanism for generating a control signal based on the detected presence of the detachable detector;
   a unit for using the generated control signal to control the drive speed of the mobile base;
   wherein the drive speed is one of full speed when the detachable detector is resting in the parking mechanism, slow speed when the detachable detector is not resting in the parking mechanism or not within a predetermined distance from the parking mechanism.

2. The mobile digital system of claim 1, wherein the presence of the detachable detector is an indication of proximity to the parking mechanism.

3. The mobile digital system of claim 2, wherein proximity to the parking mechanism is one of resting in the parking mechanism, within a predetermined distance from the parking mechanism, not resting in the parking mechanism, or not within a predetermined distance from the parking mechanism.

4. The mobile digital system of claim 3, wherein the unit for detecting the presence of the detachable detector can be any form of sensor or switch which utilizes mechanical, electromechanical, optical, capacitive, infrared or pressure to become engaged.

5. The mobile digital system of claim 4, wherein the control signal is to control the power state of the detachable detector.

6. The mobile digital system of claim 5, wherein the control signal sets the detachable detector to an ON, OFF, or Idle operating mode.

7. The mobile digital system of claim 6, wherein the power state is one of off state when the detachable detector is resting in the parking mechanism, idle state when the detachable detector is resting in the parking mechanism or within a predetermined distance from the parking mechanism, on state when the detachable detector is not resting in the parking mechanism or not within a predetermined distance from the parking mechanism.

8. The mobile digital system of claim 5, the system further comprising:
   a network adapter for coupling the mobile digital imaging system with a network.

9. The mobile digital system of claim 8, wherein the network adapter is an ethernet adapter.

10. The mobile digital system of claim 9, wherein the network adapter is a wireless adapter.

11. The mobile digital system of claim 10, wherein the detector is one of x-ray, ultrasound, or patient monitoring device.

12. A method for controlling a mobile digital imaging system the method comprising:
   providing a mobile base unit having a parking mechanism for holding a detachable detector, wherein the mobile base unit has one or more drive speed;
   detecting the presence of the detachable detector in the parking mechanism; and
   generating a control signal based on the presence of the detachable detector in the parking mechanism;
   wherein the control signal controls the power state of the detachable detector;
   wherein the control signal controls the drive speed of the mobile base unit;
   wherein the detector is one of x-ray, ultrasound, or patient monitoring device;
   wherein the drive speed is one of full speed when the detachable detector is resting in the parking mechanism, slow speed when the detachable detector is not resting in the parking mechanism or not within a predetermined distance from the parking mechanism.

13. The method for controlling a mobile digital imaging system of claim 12, wherein the presence of the detachable detector is an indication of proximity to the parking mechanism.

14. The method for controlling a mobile digital imaging system of claim 13, wherein proximity to the parking mechanism is one of resting in the parking mechanism, within a predetermined distance from the parking mechanism, not resting in the parking mechanism, or not within a predetermined distance from the parking mechanism.

15. The method for controlling a mobile digital imaging system of claim 14, wherein the unit for detecting the presence of the detachable detector can be any form of sensor or switch which utilizes mechanical, electromechanical, optical, capacitive, infrared or pressure to become engaged.

16. The method for controlling a mobile digital imaging system of claim 15, wherein the control signal is to control the power state of the detachable detector to an ON, OFF, or Idle power state.

17. The method for controlling a mobile digital imaging system of claim 16, wherein the power state is one of off state when the detachable detector is resting in the parking mechanism, idle state when the detachable detector is resting in the parking mechanism or within a predetermined distance from the parking mechanism, on state when the detachable detector is not resting in the parking mechanism or not within a predetermined distance from the parking mechanism.

* * * * *